United States Patent [19]

Lutz et al.

[11] 4,044,264

[45] Aug. 23, 1977

[54] X-RAY DIAGNOSTIC INSTALLATION FOR RADIOSCOPY AND EXPOSURES

[75] Inventors: Herbert Lutz, Seukendorf; Rolf Pfeifer, Erlangen; Hans Sausen, Bad Neuenahr-Ahrweiler, all of Germany

[73] Assignee: Siemens Aktiengesellschaft, Berlin & Munich, Germany

[21] Appl. No.: 543,054

[22] Filed: Jan. 22, 1975

[30] Foreign Application Priority Data

Jan. 22, 1974 Germany .............................. 2404937

[51] Int. Cl.² ............................................. H05G 1/30
[52] U.S. Cl. ................................ 250/409; 250/416 R
[58] Field of Search ............... 250/416, 408, 409, 401, 250/402

[56] References Cited

U.S. PATENT DOCUMENTS 3,546,461  12/1970  Craig ..................................... 250/416

Primary Examiner—Craig E. Church
Attorney, Agent, or Firm—Hill, Gross, Simpson, Van Santen, Steadman, Chiara & Simpson

[57] ABSTRACT

An X-ray diagnostic installation employed for fluoroscopy and exposures, wherein the prevailing exposure voltage may be determined by a user. The output signal of a function generator controls an arrangement for indication of the prevailing exposure voltage. This indication may be effectuated by means of a digital recording arrangement. In an embodiment of the invention, a transmission arrangement between the output of the function generator and the input of a digital recording arrangement, may comprise a coding device for the output signals. Additionally, the installation also has a construction necessitating relatively low power requirements between the X-ray diagnostic apparatus and a remotely located control panel by providing a coding and decoding arrangement intermediate the coding device and the digital recording arrangement.

2 Claims, 1 Drawing Figure

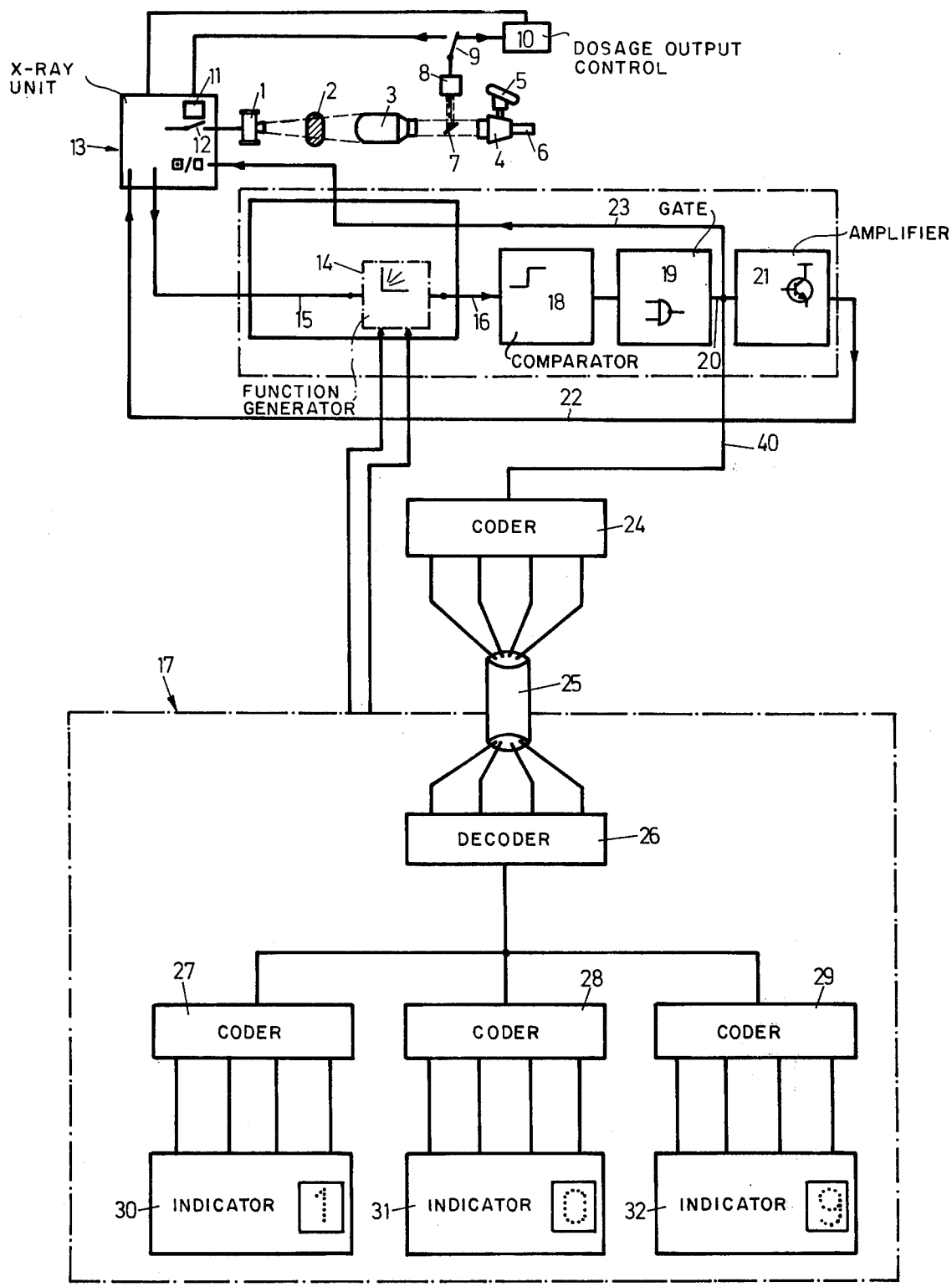

X-RAY DIAGNOSTIC INSTALLATION FOR RADIOSCOPY AND EXPOSURES

FIELD OF THE INVENTION

The present invention relates to an X-ray diagnostic installation employed for fluoroscopy and exposures.

DISCUSSION OF THE PRIOR ART

In copending U.S. Pat. application No. 394,887 (now U.S. Pat. No. 3,991,314 issued November 9, 1976), there is described an X-ray diagnostic apparatus which is utilized for fluoroscopy and for exposures, including an image amplifier-video-circuit; an arrangement for regulating the dosage output during fluoroscopy; means for determination of the exposure data from the fluoroscopic data; an automatic illuminating device; as well as a function generator which has a signal transmitted thereto in conformance with the existent fluoroscopic voltage and from which it forms an output signal for controlling the adjusting means for the exposure data and in which there is programmed the sequence of the exposure voltage in dependence upon the fluoroscopy voltage. In this X-ray diagnostic apparatus, the setting of the particular exposure voltage is carried out fully automatically. However, the possibility still remains that the user may exert an effect over the adjusted exposure voltage by means of the function generator, meaning in essence, determining the cycle of the exposure voltage in dependence upon the fluoroscopy voltage.

There is thus afforded the user the possibility of determining the characteristic of an exposure from merely a control panel. However, he still does not know which exposure voltage currently sets itself. For the control of the X-ray diagnostic apparatus it is, however, frequently desirable that the user be informed as to the currently set exposure voltage.

SUMMARY OF THE INVENTION

Accordingly, it is an object of the present invention to provide an X-ray diagnostic installation of the above-mentioned type, wherein the currently set exposure voltage may be determined by the user.

The foregoing object is attained in an inventive manner in that the output signal of the function generator controls an arrangement for indication of the presently set exposure voltage. This indication may, for example, be effectuated by means of a digital recording arrangement.

Furthermore, in an embodiment of the invention, the transmission arrangement between the output of the function generator and the input of the digital recording arrangement, may comprise a coding device for the output signals. Additionally, the installation according to the invention also has a construction necessitating relatively low power requirements between the X-ray diagnostic apparatus and a remotely located control panel by providing a coding and decoding arrangement intermediate the coding device and the digital recording arrangement.

BRIEF DESCRIPTION OF THE DRAWINGS

Further advantages and details of the invention may now be ascertained from the following description of an exemplary embodiment thereof, taken in conjunction with the single FIGURE of the accompanying drawing which illustrates a schematic circuit diagram of an X-ray diagnostic installation.

DETAILED DESCRIPTION

Referring now in detail to the drawing, there is disclosed an X-ray tube 1 which irradiates a patient 2, and then transmits from the latter an X-ray picture through an X-ray image amplifier 3 to an optical divider 4 which facilitates that the X-ray image be recorded by either a film camera 5, or a video camera 6. Located between the output of the image amplifier 3 and the optical divider 4 is a mirror 7, which convey a portion of the light radiation or beam which is present between the image amplifier 3 and the optical divider 4 to a photomultiplier 8. Through intermediary of a switch 9, the photomultiplier 8 is adapted to be connected to a dosage output control arrangement 10 during a fluoroscopic sequence, and to an automatic exposure timer 11 during an X-ray exposure. During the fluoroscopic sequence, the dosage output control arrangement 10 maintains the brightness on the output screen of the image amplifier at a constant level, whereas the automatic exposure timer 11 terminates an exposure through intermediary of a switch 12 upon achieving an optimum film darkening. The elements 11 and 12 are, respectively, constructional components of a schematically represented X-ray apparatus 13. The X-ray apparatus 13 incorporates means for the setting of the fluoroscopic and of the exposure voltages. The fluoroscopic voltage is automatically set by means of the dosage output control arrangement 10. A signal, which corresponds to the currently set fluoroscopic voltage is transmitted through a connector 15 to a function generator 14. Programmed in the function generator 14 are various programs, in accordance with which the voltage at the output 16 depends upon the voltage at the input 15. The current program is selectable at an operating or control panel 17 in a manner as is described in greater detail in copending U.S. Pat. Application No. 394,887. The output voltage of the function generator 14 is conveyed to a comparator 18, the latter of which operates in conjunction with a logic or computer element 19. Connectors 40 are connected to the output 20 of the logic element 19, whose quantity is equal to the number of preselected voltage steps for the exposure voltage.

The constructional components 18 and 19 are so formed that, for example, at a utilization of nine voltage steps or increment for the exposure voltage, corresponding to respectively, 52, 60, 70, 77, 85, 96, 102, 109 and 127 kV, there is currently applied a signal to one of the nine connectors 40, which characterizes the to be currently set exposure voltage. The setting of the exposure voltage is carried out by means of relay switches across an amplifier 21 and a connector 22 in the X-ray apparatus 13, which select corresponding tapoffs of a high voltage transformer, or of a stepping transformer which precedes the latter. The output 20 of the logic element 19 additionally is connected through a connector 23 with the X-ray apparatus 13, through which there may be selected the presently required focus for the X-ray tube 1.

The function generator 14, through the components 18 through 21, for each fluoroscopic voltage sets an associated exposure voltage in conformance with the preselected program. Upon transition from a fluoroscopic sequence to an exposure, meaning, at the reversal of switch 9, there is thus already set the particular correct exposure voltage.

It is also frequently desired to be able to determine the currently set exposure voltage. For this purpose, the nine connectors 40 may be conducted to a coding installation 24, which converts the output signals into a four-position BCD-code. For the transmission of the signals conforming to the currently set exposure voltage, there are, accordingly, required four connectors which lead, by means of a cable 25, to a decoding installation 26 in the control panel 17. The decoding installation 26, at its output, is again provided with nine connectors from which there is presently conveyed one signal which characterizes the currently set exposure voltage. The output signals of the decoding installation 26 are transmitted to three coding installations 27 through 29 which convert these signals into four-position binary signals (BCD-code). These binary signals are then transmitted to recording arrangements 30 to 32. In the illustrated embodiment of the invention, the recording installation 30 represents hundreds, the recording installation 31 represents tens, and the recording installation 32 single digits. In the illustrated exemplary embodiment there is currently indicated that at present there is available an exposure voltage of 109 kV. By means of the coding installation 27 there is effected that no indication is carried out on the recording installation 30 when only a two-digit kV number is to be indicated.

The user of the X-ray diagnostic installation thus may be at all times informed by the recording installation 30 to 32 as to which exposure voltage has been set.

As a result of the coding of the coding installation 24, and the decoding in the decoding installation 26, in lieu of nine connectors, in the illustrated exemplary embodiment only four connectors are necessary for the transmission of the digital information corresponding to the currently set exposure voltage. Within the scope of the invention, the structural components 24 and 26 may also be deleted when there is available a correspondingly high number of connectors.

The recording installations 30 to 32 are generally known digital recording or indicating installations which are controllable by means of binary signals being applied to their inputs for effecting the indication of the digit or number corresponding to the instantly applied signal. The selection of the particular desired program in the function generator 14, in accordance with which the exposure voltage depends upon the fluoroscopic voltage, is effected from control panel 17 by means of suitable operating elements (not shown).

While there has been shown what is considered to be the preferred embodiment of the invention, it will be obvious that modifications may be made which come within the scope of the disclosure of the specification.

What is claimed is:

1. In an X-ray diagnostic installation for fluoroscopy and exposures including an x-ray tube and an X-ray image amplifier; an arrangement for regulating the dosage output of said tube during fluoroscopy; means for determining the tube's exposure voltage from the tube's fluoroscopic voltage; an automatic exposure timer; and a function generator receiving an input signal corresponding to the prevailing fluoroscopic voltage, said function generator generating an analog output signal from said input signal for controlling determining means for the exposure voltage, said function generator having a plurality of the exposure voltages programmed therein dependent upon the fluoroscopic voltage, the improvement comprising: means for digitizing said analog output signal and an arrangement including a digital indicator for remotely indicating the prevailing exposure voltage as a numerical value, said arrangement being controlled by the analog output of said function generator, said digitizing means including a plurality of output connectors corresponding to a predetermined number of exposure voltage increments, a binary signal being applied to respectively one said output connector characterizing a prevailing exposure voltage increment; a coding arrangement being connected to each said indicating arrangement for each digit, said coding arrangement being controlled by the signals in said output connectors.

2. An X-ray diagnostic installation as claimed in claim 1, comprising a coding and decoding installation connected between the output of said digitizing means and the input of said coding arrangement, said coding and decoding installation converting the output signals of said digitizing means into BCD-code signals and reconverting said code signals into signals corresponding to the output signals of said digitizing means.

* * * * *